(12) United States Patent
Baril et al.

(10) Patent No.: US 11,160,543 B2
(45) Date of Patent: Nov. 2, 2021

(54) MAGNETIC SUTURE TAB FOR FREE STANDING SPECIMEN BAG

(71) Applicant: Covidien LP, Mansfield, MA (US)

(72) Inventors: Jacob C. Baril, Norwalk, CT (US); Saumya Banerjee, Hamden, CT (US)

(73) Assignee: Covidien LP, Mansfield, MA (US)

( * ) Notice: Subject to any disclaimer, the term of this patent is extended or adjusted under 35 U.S.C. 154(b) by 87 days.

(21) Appl. No.: 16/789,563

(22) Filed: Feb. 13, 2020

(65) Prior Publication Data

US 2021/0251619 A1 Aug. 19, 2021

(51) Int. Cl.
A61B 17/00 (2006.01)

(52) U.S. Cl.
CPC ........... *A61B 17/00234* (2013.01); *A61B 2017/00287* (2013.01); *A61B 2017/00876* (2013.01)

(58) Field of Classification Search
CPC ............ A61B 17/00234; A61B 17/221; A61B 2017/00287; A61B 2017/00358; A61B 2017/2212
See application file for complete search history.

(56) References Cited

U.S. PATENT DOCUMENTS

| | | | |
|---|---|---|---|
| 6,059,793 A | 5/2000 | Pagedas | |
| 6,156,055 A | 12/2000 | Ravenscroft | |
| 6,162,209 A | 12/2000 | Gobron et al. | |
| 6,171,317 B1 | 1/2001 | Jackson et al. | |
| 6,206,889 B1 | 3/2001 | Bennardo | |
| 6,224,612 B1 | 5/2001 | Bates et al. | |
| 6,228,095 B1 | 5/2001 | Dennis | |
| 6,248,113 B1 | 6/2001 | Fina | |
| 6,258,102 B1 | 7/2001 | Pagedas | |
| 6,264,663 B1 | 7/2001 | Cano | |
| 6,270,505 B1 | 8/2001 | Yoshida et al. | |
| 6,280,451 B1 | 8/2001 | Bates et al. | |
| 6,344,026 B1 | 2/2002 | Burbank et al. | |
| 6,350,266 B1 | 2/2002 | White et al. | |
| 6,350,267 B1 | 2/2002 | Stefanchik | |
| 6,358,198 B1 | 3/2002 | Levin et al. | |
| 6,368,328 B1 | 4/2002 | Chu et al. | |
| 6,383,195 B1 | 5/2002 | Richard | |
| 6,383,197 B1 | 5/2002 | Conlon et al. | |

(Continued)

*Primary Examiner* — Mohamed G Gabr
(74) *Attorney, Agent, or Firm* — Carter, DeLuca & Farrell LLP

(57) ABSTRACT

A tissue specimen retrieval bag assembly includes a tissue specimen bag having an open proximal end including a cuff defined therein and extending around a periphery thereof, a closed distal end and a bag brim disposed within the cuff. The bag brim includes a cross section configured to facilitate furling the tissue specimen bag onto itself around the bag brim to approximate a tissue specimen contained within the bag for morcellation. The tissue specimen bag also includes a suture operably disposed within the cuff. The suture includes a cinch tab operably engaged with an end of the suture to facilitate cinching the tissue specimen bag by pulling the suture away from the tissue specimen bag to cinch the tissue specimen bag to secure the tissue specimen therein. The cinch tab includes a magnetic material attracted to a metallic portion of a surgical instrument, wherein introducing the surgical instrument into the operating cavity attracts the cinch tab facilitating location thereof.

16 Claims, 4 Drawing Sheets

(56) References Cited

U.S. PATENT DOCUMENTS

| | | |
|---|---|---|
| 6,387,102 B2 | 5/2002 | Pagedas |
| 6,406,440 B1 | 6/2002 | Stefanchik |
| 6,409,733 B1 | 6/2002 | Conlon et al. |
| 6,447,523 B1 | 9/2002 | Middleman et al. |
| 6,530,923 B1 | 3/2003 | Dubrul et al. |
| 6,537,273 B1 | 3/2003 | Sosiak et al. |
| 6,752,822 B2 | 6/2004 | Jespersen |
| 6,805,699 B2 | 10/2004 | Shimm |
| 6,951,533 B2 | 10/2005 | Foley |
| 6,986,774 B2 | 1/2006 | Middleman et al. |
| 7,037,275 B1 | 5/2006 | Marshall et al. |
| 7,052,501 B2 | 5/2006 | McGuckin, Jr. |
| 7,087,062 B2 | 8/2006 | Dhindsa |
| 7,101,379 B2 | 9/2006 | Gregory, Jr. et al. |
| 7,101,380 B2 | 9/2006 | Khachin et al. |
| 7,112,172 B2 | 9/2006 | Orban, III et al. |
| 7,115,125 B2 | 10/2006 | Nakao et al. |
| 7,144,400 B2 | 12/2006 | Byrum et al. |
| 7,169,154 B1 | 1/2007 | Que et al. |
| 7,229,418 B2 | 6/2007 | Burbank et al. |
| 7,285,126 B2 | 10/2007 | Sepetka et al. |
| 7,316,692 B2 | 1/2008 | Huffmaster |
| 7,357,801 B2 | 4/2008 | Burbank et al. |
| 7,534,252 B2 | 5/2009 | Sepetka et al. |
| 7,547,310 B2 | 6/2009 | Whitfield |
| 7,615,013 B2 | 11/2009 | Clifford et al. |
| 7,618,437 B2 | 11/2009 | Nakao |
| 7,654,283 B2 | 2/2010 | Seto et al. |
| 7,670,346 B2 | 3/2010 | Whitfield |
| 7,678,118 B2 | 3/2010 | Bates et al. |
| 7,722,626 B2 | 5/2010 | Middleman et al. |
| 7,727,227 B2 | 6/2010 | Teague et al. |
| 7,731,722 B2 | 6/2010 | Lavelle et al. |
| 7,731,723 B2 | 6/2010 | Kear et al. |
| 7,762,959 B2 | 7/2010 | Bilsbury |
| 7,762,960 B2 | 7/2010 | Timberlake et al. |
| 7,875,038 B2 | 1/2011 | Que et al. |
| 7,892,242 B2 | 2/2011 | Goldstein |
| 7,914,540 B2 | 3/2011 | Schwartz et al. |
| 7,918,860 B2 | 4/2011 | Leslie et al. |
| 7,955,292 B2 | 6/2011 | Leroy et al. |
| 8,057,485 B2 | 11/2011 | Hollis et al. |
| 8,075,567 B2 | 12/2011 | Taylor et al. |
| 8,118,816 B2 | 2/2012 | Teague |
| 8,152,820 B2 | 4/2012 | Mohamed et al. |
| 8,172,772 B2 | 5/2012 | Zwolinski et al. |
| 8,211,115 B2 | 7/2012 | Cheng et al. |
| 8,231,527 B2 | 7/2012 | Beckman et al. |
| 8,282,572 B2 | 10/2012 | Bilsbury |
| 8,337,510 B2 | 12/2012 | Rieber et al. |
| 8,348,827 B2 | 1/2013 | Zwolinski |
| 8,409,112 B2 | 4/2013 | Wynne et al. |
| 8,409,216 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,486,087 B2 | 7/2013 | Fleming |
| 8,512,351 B2 | 8/2013 | Teague |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,956,370 B2 | 2/2015 | Taylor et al. |
| 8,968,329 B2 | 3/2015 | Cabrera |
| 8,986,321 B2 | 3/2015 | Parihar et al. |
| 9,005,215 B2 | 4/2015 | Grover et al. |
| 9,017,328 B2 | 4/2015 | Bahney |
| 9,017,340 B2 | 4/2015 | Davis |
| 9,033,995 B2 | 5/2015 | Taylor et al. |
| 9,084,588 B2 | 7/2015 | Farascioni |
| 9,101,342 B2 | 8/2015 | Saleh |
| 9,113,848 B2 | 8/2015 | Fleming et al. |
| 9,113,849 B2 | 8/2015 | Davis |
| 9,308,008 B2 | 4/2016 | Duncan et al. |
| 9,364,201 B2 | 6/2016 | Orban, III |
| 9,364,202 B2 | 6/2016 | Menn et al. |
| 9,370,341 B2 | 6/2016 | Ceniccola et al. |
| 9,370,378 B2 | 6/2016 | O'Prey et al. |
| 9,375,224 B2 | 6/2016 | Jansen |
| 9,414,817 B2 | 8/2016 | Taylor et al. |
| 9,468,542 B2 | 10/2016 | Hurley et al. |
| 9,486,188 B2 | 11/2016 | Secrest et al. |
| 9,522,034 B2 | 12/2016 | Johnson et al. |
| 9,549,747 B2 | 1/2017 | Carlson |
| 9,579,115 B2 | 2/2017 | Kahle et al. |
| 9,592,067 B2 | 3/2017 | Hartoumbekis |
| 9,622,730 B2 | 4/2017 | Farascioni |
| 9,624,638 B2 | 4/2017 | Lebreton et al. |
| 9,629,618 B2 | 4/2017 | Davis et al. |
| 9,655,644 B2 | 5/2017 | Collins |
| 9,730,716 B2 | 8/2017 | Secrest et al. |
| 9,789,268 B2 | 10/2017 | Hart et al. |
| 9,808,228 B2 | 11/2017 | Kondrup et al. |
| 9,826,997 B2 | 11/2017 | Cherry et al. |
| 9,867,600 B2 | 1/2018 | Parihar et al. |
| 9,877,893 B2 | 1/2018 | Taylor et al. |
| 2004/0267096 A1 | 12/2004 | Caldwell et al. |
| 2007/0073251 A1 | 3/2007 | Zhou et al. |
| 2009/0182292 A1* | 7/2009 | Egle ............... A61B 17/00234 604/327 |
| 2010/0219091 A1 | 9/2010 | Turner |
| 2011/0190779 A1 | 8/2011 | Gell et al. |
| 2017/0325798 A1 | 11/2017 | Prior |
| 2017/0325800 A1 | 11/2017 | Prior |
| 2019/0142456 A1* | 5/2019 | Wachli ............ A61B 17/32002 600/204 |

* cited by examiner

MAGNETIC SUTURE TAB FOR FREE STANDING SPECIMEN BAG

BACKGROUND

Technical Field

The present disclosure relates to tissue specimen retrieval from an internal body cavity and, more particularly, to specimen retrieval or specimen containment bags that facilitate retrieval of a tissue specimen from an internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which an access device is inserted.

Minimally-invasive surgical procedures may be used for partial or total retrieval of a tissue specimen from an internal body cavity. However, the restricted access provided by minimally-invasive openings (natural passageways and/or surgically created openings) presents challenges with respect to maneuverability and visualization. The restricted access also presents challenges when the tissue specimen is required to be removed. As such, a tissue specimen that is deemed too large for intact retrieval may be broken down into a plurality of smaller pieces to facilitate retrieval from the internal body cavity.

During such minimally-invasive surgical procedures, it is common that a cyst, tumor, or other affected tissue specimen is required to be removed. In these and other procedures where cancerous tissue is required to be removed, retrieval of the tissue specimen in an enclosed environment such as a specimen retrieval bag or containment bag is highly desirable to inhibit seeding of cancer cells. Thus, with respect to breaking down large tissue specimens for retrieval through minimally-invasive openings, there is the added challenge of doing so within an enclosed environment.

In these instances, a standalone tissue bag may be utilized to contain large tissue specimens such as a uterus for hysterectomies or fibroids for myomectomies. The specimen retrieval bag or containment bag typically includes a bag brim having a flexible wire support that is transitionable between a first collapsed configuration for insertion through an incision or natural body orifice and a second expanded configuration for encapsulating tissue specimens. The bag brim, once externalized, may be manipulated or rolled to enhance surgical access to the tissue specimen or "tent" the specimen as needed.

SUMMARY

As used herein, the term "distal" refers to the portion that is described which is further from a user, while the term "proximal" refers to the portion that is being described which is closer to a user. The terms "substantially" and "approximately," as utilized herein, account for industry-accepted material, manufacturing, measurement, use, and/or environmental tolerances. Further, any or all of the aspects and features described herein, to the extent consistent, may be used in conjunction with any or all of the other aspects and features described herein.

In accordance with aspects of the present disclosure is a tissue specimen retrieval bag assembly which includes a tissue specimen bag having an open proximal end including a cuff defined therein and extending around a periphery thereof, a closed distal end and a bag brim disposed within the cuff. The bag brim includes a cross section configured to facilitate furling the tissue specimen bag onto itself around the bag brim to approximate a tissue specimen contained within the bag for morcellation. The tissue specimen bag also includes a suture operably disposed within the cuff. The suture includes a cinch tab operably engaged with an end of the suture to facilitate cinching the tissue specimen bag by pulling the suture away from the tissue specimen bag to cinch the tissue specimen bag to secure the tissue specimen therein. The cinch tab includes a magnetic material attracted to a metallic portion of a surgical instrument, wherein introducing the surgical instrument into the operating cavity attracts the cinch tab facilitating location thereof.

In aspects according to the present disclosure, the cinch tab is made from a magnetic material. In other aspects according to the present disclosure, the cinch tab includes a base material having a magnetic material deposited thereon. In yet other aspects according to the present disclosure, the magnetic material deposited atop the base material is in the shape of indicia.

In aspects according to the present disclosure, the cinch tab includes a magnetic material having a second material overmolded thereon. In other aspects according to the present disclosure, the cinch tab includes a geometry to facilitate handling thereof.

In aspects according to the present disclosure, the cinch tab includes a grommet defined therein configured to operably engage the suture. In other aspects according to the present disclosure, the cinch tab is configured to slide atop the suture to lock the tissue specimen bag when cinched.

In accordance with additional aspects of the present disclosure is a tissue specimen retrieval bag assembly which includes a tissue specimen bag having an open proximal end including a cuff defined therein and extending around a periphery thereof, a closed distal end and a bag brim disposed within the cuff. The tissue specimen bag also includes a suture operably disposed within the cuff. The suture includes a cinch tab operably engaged with an end of the suture to facilitate cinching the tissue specimen bag by pulling the suture away from the tissue specimen bag to cinch the tissue specimen bag to secure the tissue specimen therein. The cinch tab includes a magnetic material attracted to a metallic portion of a surgical instrument, wherein introducing the surgical instrument into the operating cavity attracts the cinch tab facilitating location thereof.

In aspects according to the present disclosure, the cinch tab is made from a magnetic material. In other aspects according to the present disclosure, the cinch tab includes a base material having a magnetic material deposited thereon. In yet other aspects according to the present disclosure, the magnetic material deposited atop the base material is in the shape of indicia.

In aspects according to the present disclosure, the cinch tab includes a magnetic material having a second material overmolded thereon. In other aspects according to the present disclosure, the cinch tab includes a geometry to facilitate handling thereof.

In aspects according to the present disclosure, the cinch tab includes a grommet defined therein configured to operably engage the suture. In other aspects according to the present disclosure, the cinch tab is configured to slide atop the suture to lock the tissue specimen bag when cinched.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1A:
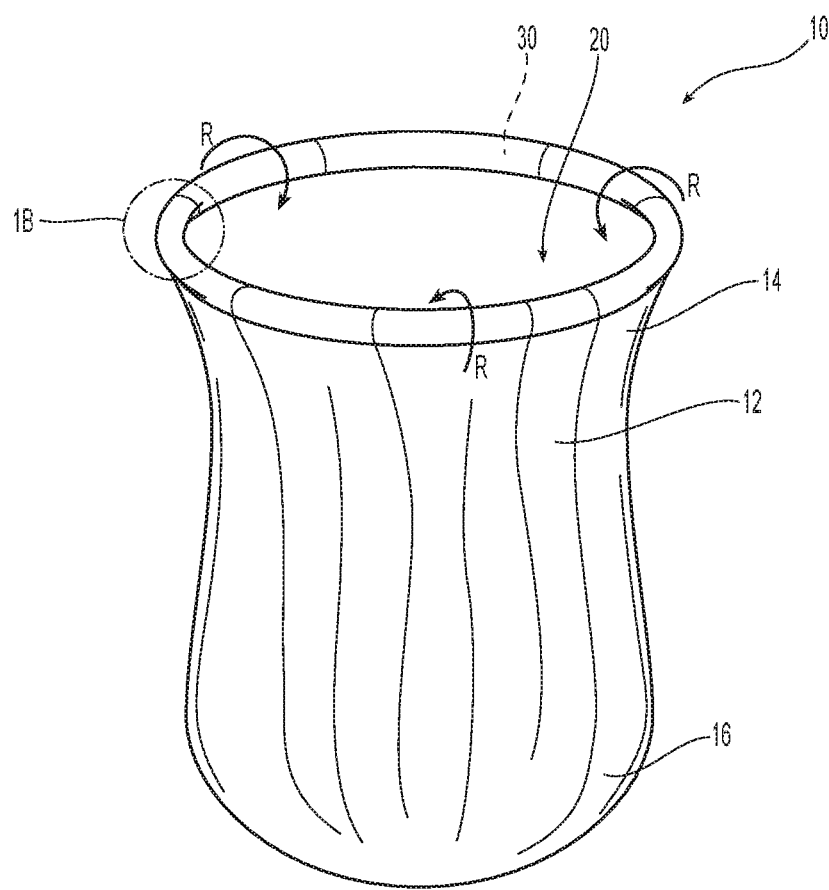
FIG. 1A is a perspective view of a tissue specimen bag provided in accordance with aspects of the present disclosure.
Figure 1B:
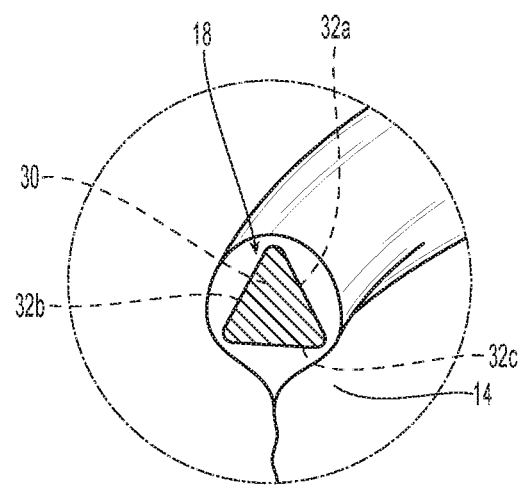
FIG. 1B is a perspective cross sectional view of a proximal end of the tissue specimen bag of FIG. 1A.

Turning initially to FIGS. 1A-1B, one embodiment of a standalone tissue specimen retrieval bag or tissue containment bag assembly is shown and is represent by reference numeral 10. Bag assembly 10 includes a bag 12 having a proximal end 14 including an opening 20 defined therein and an enclosed distal end 16. Bag assembly 10 includes bag rim 30 that is configured to support bag 12 in such a fashion as to define opening 20 when the bag 12 is unfurled or in an open configuration. Opening 20 is of sufficient dimension to receive one or more tissue specimens "T" during a particular surgical procedure. Bag assembly 10 may be made from nylon and/or polyurethane.

Bag rim 30 is configured to be flexible such that the bag brim 30 is easily transitionable between a first, collapsed configuration wherein the bag 12 is furled (as explained below) and a second, expanded configuration which allows the bag 12 to be unfurled for receipt of a tissue specimen "T". As such, bag brim 30 may be made from any flexible material that is easily expandable from a collapsed configuration. Bag 12 may include any suitable rollable material such as nylon, polyurethane, etc.

Bag brim 30 is configured to seat within an elongated cuff 18 (FIG. 1B) defined in the proximal end of the bag 12. More particularly, bag brim 30 is of sufficient dimension to fit within the cuff 18 along an entire length thereof. Bag brim 30 may include two mating ends that, when engaged, form a generally circular configuration when opened to support bag 12 thereon. Bag brim 30 may be generally triangular in shape to include three sides 32a, 32b and 32c. Other geometric configurations or multi-sided arrangements are also envisioned and may be tailored for a particular purpose.

The generally triangular shape of the bag brim 30 allows the bag 12 to roll or furl around itself which, in turn, allows a surgeon to tent (i.e., position) the tissue specimen "T" closer to the proximal end of the operating cavity as needed for dissection. More particularly, the geometry of the sides 32a, 32b and 32c of the bag brim 30 facilitate furling/unfurling the bag 12 as needed and securing the bag 12 in a desired furled position. Although generally illustrated in the various embodiments described herein as being rolled or furled inwardly, it is contemplated that the bag 12 may be rolled either inwardly or outwardly about the bag brim 30.

In use, the specimen "T" is placed into the specimen bag 12 through opening 20. The weight of the specimen "T" causes the specimen "T" to fall to toward the distal end 16 of the bag 12. The proximal end 14 of the bag 12 and the circularly-shaped bag brim 30 maintain the proximal end 14 the bag 12 outside the operating cavity (See for example, FIG. 2). If the surgeon desires to bring the specimen "T" closer to the proximal end 14 of the bag 12, the surgeon furls the bag 12 around the bag brim 30 in the direction "R". The triangular shape of the bag brim 30 facilitates furling the bag 12 and the brim 30 over on itself which, in turn, allows the surgeon to position the tissue specimen "T" at a desired depth within the surgical cavity depending upon a particular purpose. The sides 32a, 32b and 32c of the bag brim 30 may include a high friction surface to facilitate gripping the bag 12 when furling.

Figure 2:
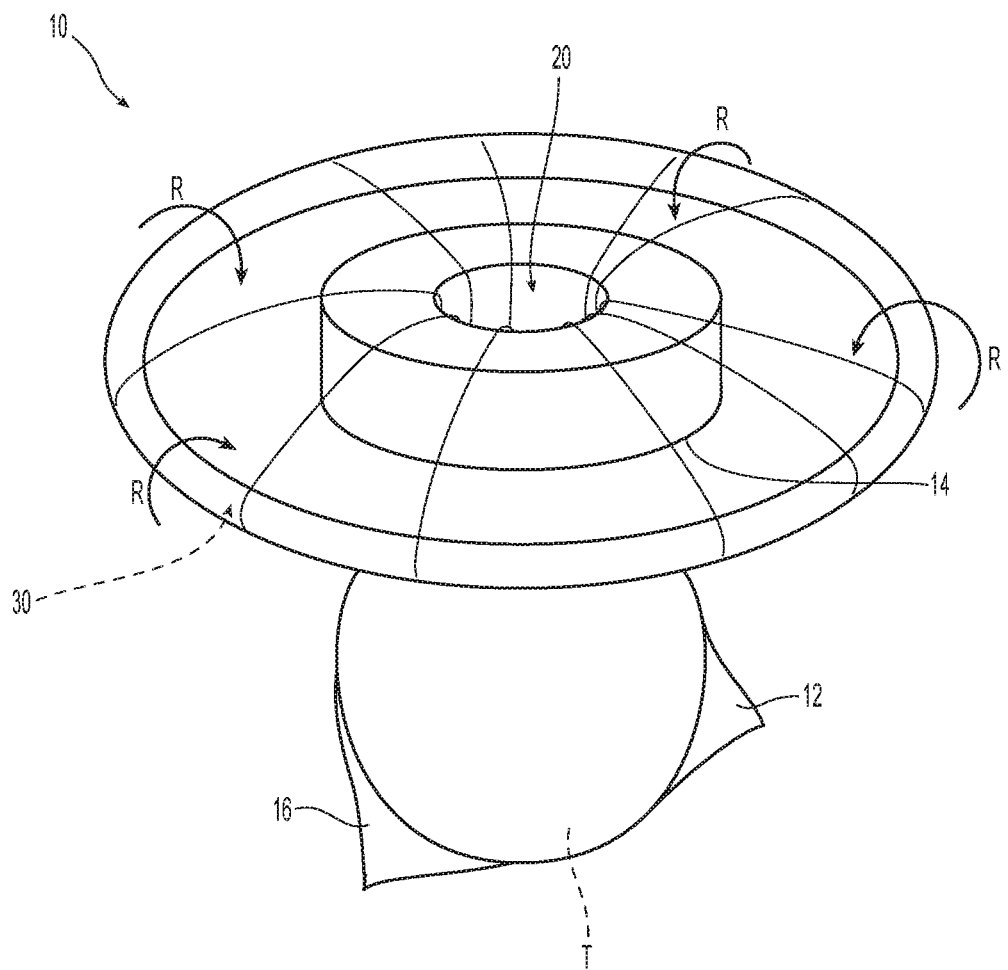
FIG. 2 is a perspective view of the tissue specimen retrieval bag having a rollable bag brim according to the present disclosure.

FIG. 2 shows the tissue specimen retrieval bag assembly 10 in use containing and supporting tissue specimens "T" within a surgical cavity. More particularly, bag assembly 10 includes a bag brim 30 having a bag 12 that depends therefrom for containing a tissue specimen "T". Bag brim 30 is disposed within a cuff (not shown) defined in a proximal end 14 of the bag 12. Bag brim 30 allows the bag 12 to roll or furl around itself which, in turn, allows a surgeon to tent (i.e., position) the tissue specimen "T" closer to the proximal end of the operating cavity as needed for dissection.

Figure 3:
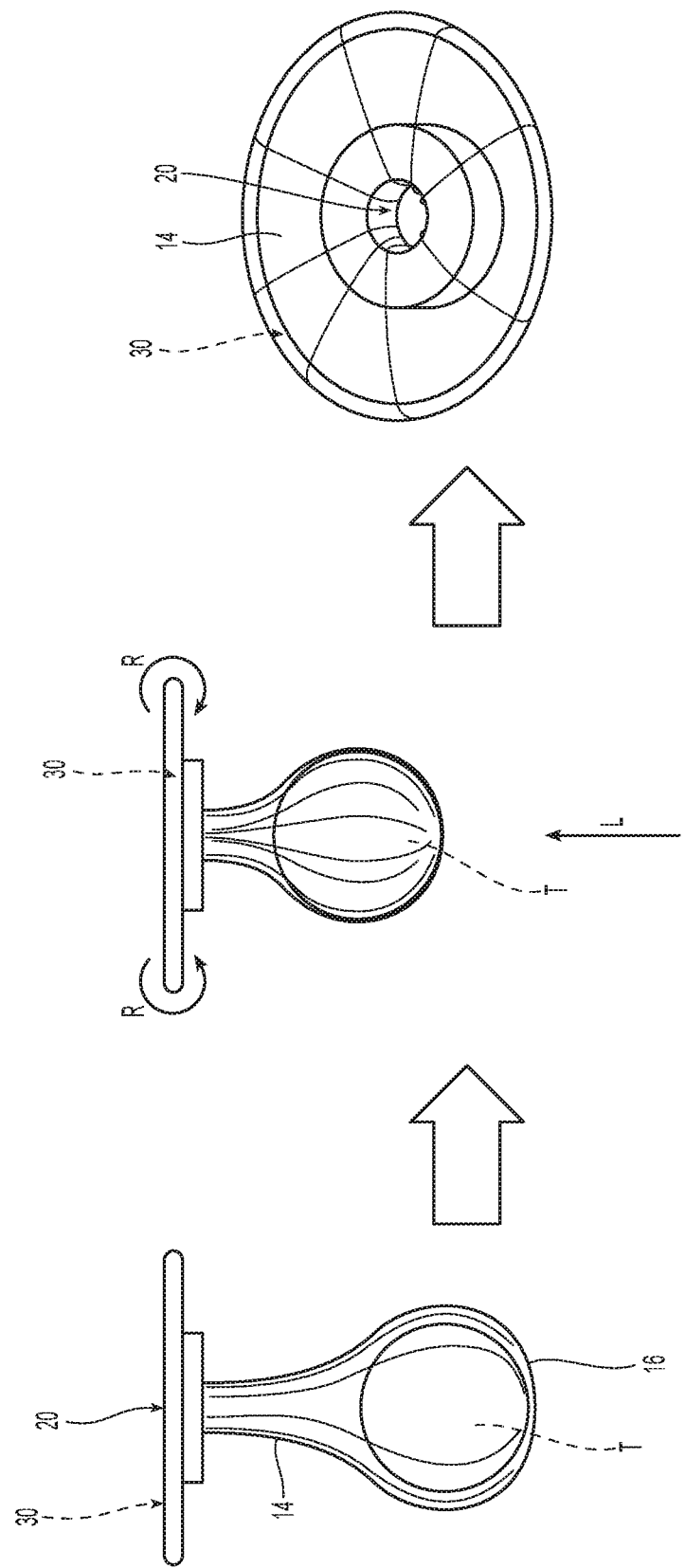
FIGS. 3A-3C are various views of the tissue specimen retrieval bag of FIG. 1 for use with a tissue specimen "T"

More particularly, and as best shown in FIGS. 3A-3C, the geometry of the sides of the bag brim 30 facilitate furling/unfurling the bag 12 as needed and securing the bag 12 in a desired furled position. As shown in FIG. 3A, the specimen "T" is place into the specimen bag 12 through opening 20. The weight of the specimen "T" causes the specimen "T" to fall to toward the distal end 16 of the bag 12. The proximal end 14 of the bag 12 and the circularly-shaped bag brim 30 maintain the proximal end 14 the bag 12 outside the operating cavity (See FIG. 3C). If the surgeon desires to bring the specimen "T" closer to the proximal end 14 of the bag 12, e.g., for morcellation purposes, the surgeon furls the bag 12 around the bag brim 30 in the direction "R". The shape of the bag brim 30 facilitates furling the bag 12 and the brim 30 over on itself which, in turn, allows the surgeon to position the tissue specimen "T" at a desired depth "L" within the surgical cavity depending upon a particular purpose (See FIG. 3B).

Figure 4:
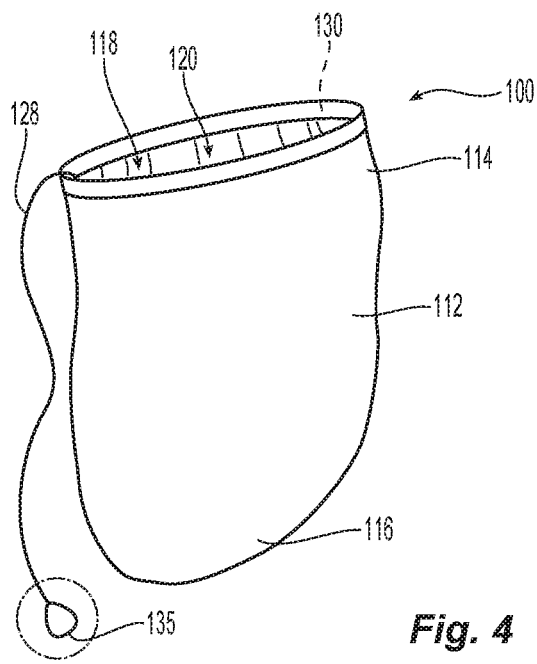
FIG. 4 is a perspective view of another embodiment of a tissue specimen retrieval bag according an embodiment of the present disclosure.
Figure 5:
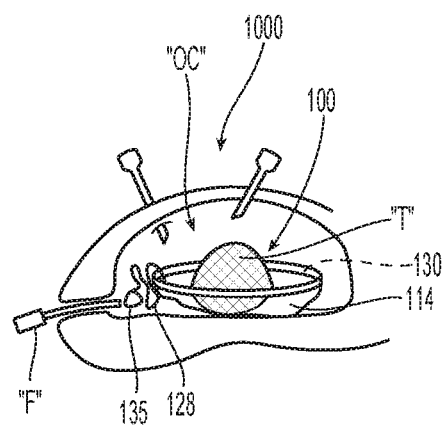
FIG. 5 is an internal, schematic view of the tissue specimen retrieval bag of FIG. 4 shown within an operating cavity.
Figure 6:
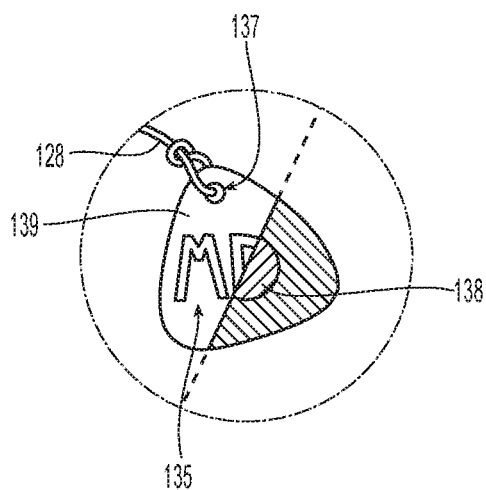
FIG. 6 is an enlarged, perspective view of a cinch tab for use with the tissue specimen retrieval bag of FIG. 4.

FIGS. 4-6 show another embodiment of tissue specimen retrieval bag assembly 100 for containing and supporting tissue specimens "T" within a surgical cavity. More particularly, bag assembly 100 includes a bag brim 130 having a tissue specimen bag 112 that depends therefrom for containing a tissue specimen "T". Bag brim 130 is disposed within a cuff 118 defined in a proximal end 114 of the bag 112. Bag brim 130 allows the bag 112 to roll or furl around itself which, in turn, allows a surgeon to tent (i.e., position) the tissue specimen "T" closer to the proximal end of the operating cavity as needed, e.g., for inspection, morcellation, dissection, etc.

Cuff 118 of bag assembly 100 is configured to house a suture 128 therein such that, after encapsulation of the tissue specimen "T", the suture 128 may be pulled to cinch the tissue specimen bag 112 to contain the specimen "T" for extraction and transport. A cinch tab 135 is utilized to facilitate pulling the suture 128 to cinch the tissue specimen bag 112 (FIG. 6). Cinch tab 135 includes a grommet 137 to reinforce the engagement between the suture 128 and the cinch tab 135.

In use and as best shown in FIGS. 4-5, a tissue specimen "T" is captured and placed within the tissue specimen bag 112 through opening 120 (FIG. 4). Additional tissue (not shown) may be added to the tissue specimen bag 112 if needed. Once all of the desired tissue is properly contained within the tissue specimen bag 112, the cinch tab 135 is located and then pulled away from the tissue specimen bag 112 to cinch the proximal end 114 of the tissue specimen bag 112. Continued pulling of the cinch tab 135 away from the tissue specimen bag 112 closes the opening 120 and readies the tissue specimen bag 112 for exteriorization.

Cinch tab 135 is made from or includes a layer of magnetic material 138 to facilitate location of the cinch tab 135 within the operating cavity "OC". More particularly and in the embodiment shown in FIG. 6, cinch tab 135 includes a layer of magnetic material 138 deposited atop a base material 139. As shown, the magnetic material 138 may be deposited atop the base material 139 as a logo or other identifying indicia. The geometry of the magnetic material 138 may be deposited atop the base material 139 and dimensioned to facilitate location of the cinch tab 135 with the operating cavity "OC". In embodiments, the entire cinch tab 135 may be made from the magnetic material 138 or any part thereof. In embodiments, an overmold material may be overmolded atop the magnetic material 138 to form the cinch tab 135.

In use and as shown in FIG. 5, once all of the desired tissue is properly contained within the tissue specimen bag 112, the surgeon introduces a metallic or ferrous instrument "F" that is attracted to the magnetic properties of the cinch tab 135 into the operating cavity to attract, hence locate, the cinch tab 135. In other words, the magnetic material 138 of the cinch tab 135 is attracted to the ferrous instrument "F" facilitating the location of the cinch tab 135 within the operating cavity "OC". Once the cinch tab 135 is located, it may be pulled away from the tissue specimen bag 112 to cinch the proximal end 114 of the tissue specimen bag 112 to secure the tissue specimen "T". The tissue specimen "T" may then be exteriorized utilizing the cinch tab 135 for leverage, e.g., in the case of transvaginal exteriorization where the natural (or recently excised) opening tends to be narrow.

After the opening 120 is completely closed, the cinch tab 135 may be slid atop the suture 128 and moved toward the tissue specimen bag 112 to lock the cinch tab 135 against the bag 112 to prevent the tissue specimen bag 112 from re-opening. The grommet 137 may be coated with a high friction material to facilitate this purpose. Alternatively, the cinch tab 135 may include a locking slit (not shown) defined therein such that, once fully seated against the tissue specimen bag 112, the suture 128 can be engaged within the slit to lock the cinch tab 135 in place atop the suture 128. The cinch tab 135 may include a loop defined therein (not shown) or geometry (e.g., triangular) configured to facilitate handling thereof. The loop or geometry may be configured and sized to fit a user's finger to enhance a user's grip and provide additional leverage for cinching.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue specimen retrieval bag assembly, comprising:
   a tissue specimen bag including:
      an open proximal end having a cuff defined therein and extending around a periphery thereof;
      a closed distal end;
      a bag brim disposed within the cuff, the bag brim having a cross section configured to facilitate furling the tissue specimen bag onto itself around the bag brim to approximate a tissue specimen contained within the bag for morcellation; and
      a suture operably disposed within the cuff, the suture including a cinch tab operably engaged with at least one end of the suture to facilitate cinching the tissue specimen bag by pulling the suture away from the tissue specimen bag to cinch the tissue specimen bag to secure the tissue specimen therein, the cinch tab including a magnetic material attracted to a metallic portion of a surgical instrument, wherein introducing the surgical instrument into the operating cavity attracts the cinch tab facilitating location thereof.

2. The tissue specimen retrieval bag assembly according to claim 1 wherein the cinch tab is made from a magnetic material.

3. The tissue specimen retrieval bag assembly according to claim 1 wherein the cinch tab includes a base material having a magnetic material deposited thereon.

4. The tissue specimen retrieval bag assembly according to claim 3 wherein the magnetic material deposited atop the base material is in the shape of indicia.

5. The tissue specimen retrieval bag assembly according to claim 1 wherein the cinch tab includes a magnetic material having a second material overmolded thereon.

6. The tissue specimen retrieval bag assembly according to claim 1 wherein the cinch tab includes a geometry to facilitate handling thereof.

7. The tissue specimen retrieval bag assembly according to claim 1 wherein the cinch tab includes a grommet defined therein configured to operably engage the suture.

8. The tissue specimen retrieval bag assembly according to claim 1 wherein the cinch tab is configured to slide atop the suture to lock the tissue specimen bag when cinched.

9. A tissue specimen retrieval bag assembly, comprising:
   a tissue specimen bag including:
      an open proximal end having a cuff defined therein and extending around a periphery thereof;
      a closed distal end;
      a bag brim disposed within the cuff; and
      a suture operably disposed within the cuff, the suture including a cinch tab operably engaged with at least one end of the suture to facilitate cinching the tissue specimen bag by pulling the suture away from the tissue specimen bag to cinch the tissue specimen bag to secure the tissue specimen therein, the cinch tab including a magnetic material associated therewith, wherein introducing a surgical instrument having at least a portion that is metal into the operating cavity attracts the cinch tab facilitating location thereof.

10. The tissue specimen retrieval bag assembly according to claim 9 wherein the cinch tab is made from magnetic material.

11. The tissue specimen retrieval bag assembly according to claim 9 wherein the cinch tab includes a base material having a magnetic material deposited thereon.

12. The tissue specimen retrieval bag assembly according to claim 11 wherein the magnetic material deposited atop the base material is in the shape of indicia.

13. The tissue specimen retrieval bag assembly according to claim 9 wherein the cinch tab includes a magnetic material having a second material overmolded thereon.

14. The tissue specimen retrieval bag assembly according to claim 9 wherein the cinch tab includes a geometry to facilitate handling thereof.

15. The tissue specimen retrieval bag assembly according to claim 9 wherein the cinch tab includes a grommet defined therein configured to operably engage the suture.

16. The tissue specimen retrieval bag assembly according to claim 9 wherein the cinch tab is configured to slide atop the suture to lock the tissue specimen bag when cinched.

* * * * *